(12) United States Patent
Lex

(10) Patent No.: US 8,928,886 B2
(45) Date of Patent: Jan. 6, 2015

(54) SURFACE MEASURING DEVICE HAVING TWO MEASURING UNITS

(75) Inventor: Konrad Lex, Koenigsdorf (DE)

(73) Assignee: BYK-Gardner GmbH (DE)

( * ) Notice: Subject to any disclaimer, the term of this patent is extended or adjusted under 35 U.S.C. 154(b) by 345 days.

(21) Appl. No.: 12/575,350

(22) Filed: Oct. 7, 2009

(65) Prior Publication Data

US 2010/0091269 A1 Apr. 15, 2010

(30) Foreign Application Priority Data

Oct. 14, 2008 (DE) .......................... 10 2008 051 513

(51) Int. Cl.
*G01N 21/55* (2014.01)
*G01B 11/30* (2006.01)
*G01N 21/57* (2006.01)

(52) U.S. Cl.
CPC ............... *G01N 21/55* (2013.01); *G01N 21/57* (2013.01)
USPC ........................................ 356/445; 356/600

(58) Field of Classification Search
None
See application file for complete search history.

(56) References Cited

U.S. PATENT DOCUMENTS

| | | | | |
|---|---|---|---|---|
| 5,923,434 | A * | 7/1999 | Lex ............................... | 356/445 |
| 6,914,684 | B1 * | 7/2005 | Bolash et al. ................. | 356/600 |
| 6,975,404 | B2 * | 12/2005 | Schwarz ........................ | 356/446 |
| 7,391,518 | B1 * | 6/2008 | Schwarz et al. ............. | 356/446 |
| 2006/0033058 | A1 * | 2/2006 | Schwarz ................... | 250/559.39 |
| 2006/0033922 | A1 * | 2/2006 | Sperling et al. ............... | 356/446 |
| 2006/0144295 | A1 * | 7/2006 | Misaki et al. ................. | 106/401 |
| 2007/0153285 | A1 * | 7/2007 | Elton et al. .................... | 356/446 |
| 2008/0013074 | A1 * | 1/2008 | Schwarz et al. ................ | 356/73 |
| 2008/0034602 | A1 * | 2/2008 | Schwarz ......................... | 33/701 |
| 2008/0231865 | A1 * | 9/2008 | Schwarz et al. ............. | 356/601 |
| 2008/0232646 | A1 * | 9/2008 | Lex ............................... | 382/108 |
| 2008/0246969 | A1 * | 10/2008 | Imura ........................... | 356/445 |
| 2009/0046300 | A1 * | 2/2009 | Schwarz et al. ............. | 356/600 |
| 2012/0026512 | A1 * | 2/2012 | Schwarz ....................... | 356/612 |
| 2014/0152990 | A1 * | 6/2014 | Ehbets et al. ................ | 356/405 |

FOREIGN PATENT DOCUMENTS

| | | | |
|---|---|---|---|
| JP | 61-145436 | | 3/1986 |
| JP | 63-295945 | | 12/1988 |
| JP | 2001146630 | A * | 5/2001 |
| JP | 2003-329586 | | 11/2003 |
| JP | 2007-033099 | | 8/2007 |
| JP | 2009-232065 | | 8/2009 |

OTHER PUBLICATIONS

Chinese Office Action issued for corresponding application No. 200910174084X, dated Nov. 7, 2012 (19 pgs).
Translation of Chinese Office Action issued for corresponding Appln. No. 200910174084X, dated Jan. 29, 2014 (6 pgs).
Translation of Japanese Action Appln No. 2009-232065 dated Jan. 8, 2014 (1 pg).

* cited by examiner

*Primary Examiner* — Gordon J Stock, Jr.
(74) *Attorney, Agent, or Firm* — Hayes Soloway P.C.

(57) ABSTRACT

An apparatus for determining optical properties of materials including a first measuring device having a first radiation device which directs radiation onto the material under a first specified angle of radiation and a first radiation detection device which is located under a first angle of reception with respect to the material, and a second measuring device which includes a second radiation device which directs radiation onto the material under a second specified angle of radiation and a second radiation detection device which is located at a second angle of reception with respect to the material and allows a locally resolved evaluation of the radiation incident thereon and emits at least one second characteristic signal which is characteristic of the radiation incident on the second radiation detection device.

21 Claims, 1 Drawing Sheet

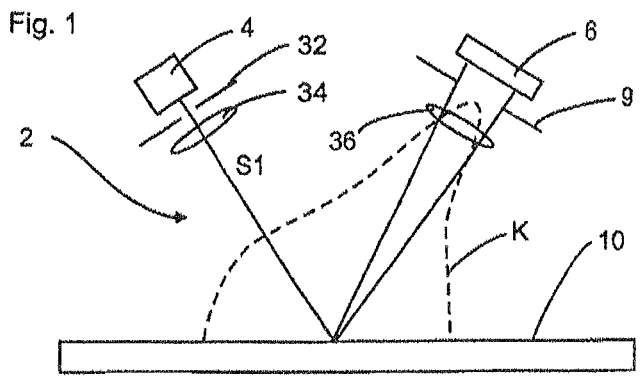
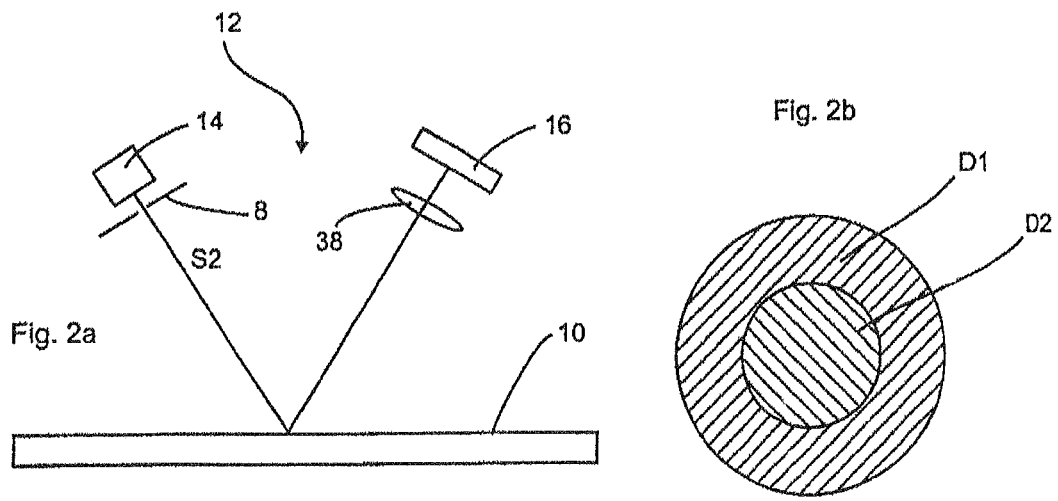
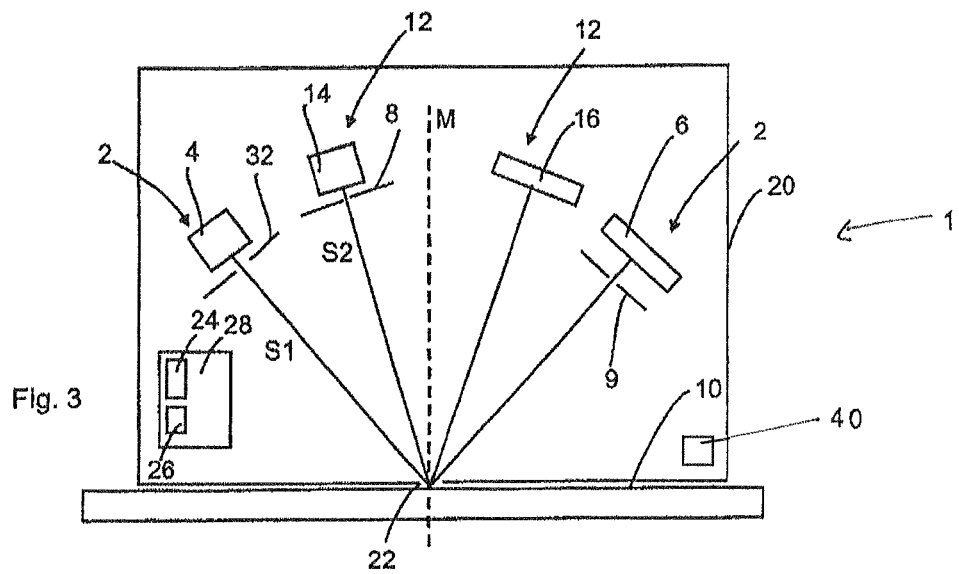

SURFACE MEASURING DEVICE HAVING TWO MEASURING UNITS

BACKGROUND OF THE INVENTION

The present invention relates to an apparatus for determining optical properties of materials and in particular optical surface properties of materials. The apparatus according to the invention and the method according to the invention will be described with reference to devices which determine the surface properties of paint coatings, in particular for vehicles. However, it is noted that the invention may also be used with other surfaces such as those of pieces of furniture.

From the prior art, various apparatus and also various measuring methods for determining surface properties are known. According to one of the known measurement methods, for example a certain object such as a diaphragm is projected across the surface onto the detector. The angle of detection here preferably corresponds to the angle of radiation. From the image which is preferably recorded by means of a camera, conclusions with regard to quality, e.g. the distinctness of image (dullness) of the surface concerned may be drawn.

In a further measurement method it is also possible to project a lighting diaphragm across the surface to be evaluated onto a detector and to receive the reflected radiation under a certain angle, preferably the angle of reflection. To this end, especially diaphragms are used, so that the quality of the surface may be evaluated also on the basis of the ratio between the radiated and the received intensity. Thus, according to this method a diaphragm is used on the detector side. This principle is also known as gloss measuring technology.

This last-mentioned measurement method is, however, also dependent on a curvature of the surface concerned. The first-mentioned measurement method is to a lesser degree influenced by the curvature of the surface.

The measurement methods mentioned are used to allow the optical impression as perceived by the user to be detected as objectively as possible. It is to be noted here that the human eye is able to perceive optical differences only subjectively and there is therefore a need to provide objective measurement apparatus and measurement methods. The above-mentioned second variant, however, is also dependent on the physical properties of the surface, such as in particular the index of refraction.

Surfaces having different indices of refraction will result here in different measurement results, simply because of the different indices of refraction. However, it may also be possible that two surfaces which optically convey exactly the same impression will still lead to different measurement results. The first-mentioned measurement method is—at least according to certain evaluation methods—not dependent on the index of refraction, but requires that sufficient light is reflected or scattered from the surface, so that an image may be received. This is very difficult particularly in the case of matt surfaces.

SUMMARY OF THE INVENTION

It is therefore the object of the present invention to provide an apparatus and a method for determining optical properties, which allow a more objective evaluation of the surfaces to be examined.

An apparatus according to the invention for determining optical properties of materials and in particular of surfaces includes a first measuring device having a first radiation device, which in turn directs radiation under a first specified angle of radiation onto the material and which further has a first radiation detection device which is disposed under a first angle of reception with respect to the material and which receives at least a proportion of the radiation directed from the first radiation device onto the material and scattered back from the material. At the same time, the first radiation detection device emits a first characteristic signal which is characteristic of the intensity of the radiation incident on the first radiation detection device.

According to the invention the apparatus includes a second measuring device having a (second) radiation device which also directs radiation under a second specified angle of radiation onto the material and which has a (second) radiation detection device which is disposed under a second angle of reception with respect to the material and which receives at least a proportion of the radiation directed onto the material by the second radiation device and scattered back from the material, with the second radiation detection device allowing a locally resolved evaluation of the incident radiation and emitting at least one second characteristic signal which is characteristic of the radiation falling on the second radiation detection device.

Thus, according to the invention it is suggested to carry out the corresponding measurements by means of two measurement methods, whereby it is possible that one measurement verifies the results of the other measurement, so that it may be determined, for example, that a certain result of the first measurement method is different only because of different indices of refraction of the surface. In this connection it is possible, as will be explained in more detail below, that one or more components of a measuring device may also be used by the other measuring device.

The backscattered radiation is in particular reflected radiation. Thus, the first radiation detection device preferably only outputs an intensity value. In this case, it is therefore not absolutely necessary to receive a locally resolved image of the incident radiation, but a comparison is made between the intensity incident on the radiation detector and the emitted intensity. On the basis of this ratio, a conclusion is drawn with regard to a quality of the surface, as was mentioned above.

By contrast, according to the last-mentioned measurement method according to the invention, a locally resolved image of the radiation incident on the measuring device is emitted, so that a conclusion may be drawn with respect to the surface in particular from this image. Or more specifically, a diaphragm across the surface may be projected onto the detector device, and this image may be examined in a locally resolved manner. In doing so, conclusions with regard to the optical property of the surface may be drawn.

In a further advantageous embodiment, the apparatus includes a processing device which outputs at least one value that is characteristic of the surface, taking into account the first characteristic signal and the second characteristic signal. It is possible here to emit during a certain measurement the characteristic value whilst taking into account only the first signal or taking into account only the second signal. It is, however, in particular also possible that the characteristic value is output for a certain measurement whilst taking into account both signals, in order to allow, as mentioned above, any distortions caused for example by a different index of refraction to be considered.

Conversely, however, it is also possible that in the case of certain surfaces, it is this different index of refraction that will also lead to different optical impressions. In this case, in particular the second measurement method described in the beginning will fail (which was, however, mentioned first within the context of the invention), since this is, as was mentioned above, not dependent on the index of refraction. In this case, however, a real result value may be determined by using the respectively second measurement method.

In a further advantageous embodiment, the first angle of radiation and the first angle of reception are disposed essentially mirror-inverted with regard to a mean perpendicular to one of the material. This means that the first measuring device will receive essentially in reflection. The material will advantageously be a surface and the radiation detection device will thus also receive at least reflected radiation. Preferably, also the second angle of radiation and the second angle of reception are essentially mirror-inverted with respect to one another.

In a further advantageous embodiment, the apparatus has a radiation detection device which is part of both measuring devices. In this case, preferably two radiation devices are thus provided, which radiate onto the material preferably under the same angle. The radiation detection device thus receives the light scattered back from the surface with regard to both radiation devices.

In a further advantageous embodiment, the apparatus includes a radiation device which is part of both measuring devices. This embodiment has the advantage that in both measurement processes, exactly the same area of the surface to be examined will be irradiated. In this case, preferably two radiation detection devices are provided, which receive the light scattered back from the surface under different angles.

In a further preferred embodiment, both a radiation device and a radiation detection device are included in both measuring devices. In this case, according to one measuring method a software diaphragm may be generated and the light may be detected integrally, and according to the other measurement method, the diaphragm image may be analysed in a locally resolved manner by means of image evaluation. Since the detection area of a corresponding CCD chip is considerably larger than the measurement area, it may be possible here in the case of tilted or curved surfaces to find the image on the camera chip, and the evaluation may be carried out in an area of the CCD chip, which is offset with regard to a base area.

Thus, what is preferably common to all of the apparatus or methods according to the invention is that an integral measurement is combined with a locally resolved measurement.

In a further advantageous embodiment, a diaphragm unit is located upstream of the first radiation detection device. By means of this diaphragm unit it may be determined which proportion of the light incident on the surface falls onto a delimited area of the radiation detection device, i.e. within the diaphragm. This diaphragm unit is preferably disposed in a fixed manner.

However, it would also be possible to realise this diaphragm in software, e.g. by establishing that only a certain area of a CCD chip is used for evaluation or that only a certain number of pixels is evaluated. In this way, different diaphragms may be realised in a particularly simple manner.

In this way, any inaccuracies or curvatures of the surface may be determined, since in the case of greater curvatures, part of the light no longer falls on the radiation detection device, but on the diaphragm, or will be scattered in all spatial directions. The flatter the surface is, the higher is the proportion of incident light that will be scattered in all spatial directions.

In a further advantageous embodiment, the apparatus includes evaluation means which analyse the second characteristic signal under determination of several different factors. For example, it is possible that a certain image is analysed for instance in the manner of a Fourier analysis, and to this end different filters may be used. It is for example possible to obtain several measurement values for a certain surface, and these will be subdivided for different spatial areas or distances of the surfaces to be examined. With regard to these individual measurement values, statistical values such as standard deviations may be output in each case, and on the basis of this subdivision the surface may be evaluated. This method is described in detail in DE 10 2006 032 404 A1, the content of which is by reference included in its entirety in the disclosure of the present application. It would be possible here that the apparatus includes an evaluation means which analyses the second signal under determination of several different factors and in particular of local filter factors.

Apart from that, the apparatus may also include further radiation devices which irradiate the surface under different angles and, if needed, also several radiation detection devices which are located opposite the surface at different angles. Here, in particular also the light scattered from the surface may be detected or evaluated. In this way, in particular colour effects may be measured.

In a further advantageous embodiment, the apparatus includes a processing means which outputs a value that is characteristic of an index of refraction of the material, taking into account the first characteristic signal and the second characteristic signal. For example, it is possible to create or take as a basis tables which allocate corresponding indices of refraction to certain first signals, wherein the respectively second signal is taken into account for the allocation and wherein it will for example be determined that this remains unchanged for two different surfaces, so that the conclusion may be drawn that the optical impression is the same, but the indices of refraction differ.

Or to be more specific, it would for example be possible to detect two different surfaces. If the second signal remains the same, the conclusion may be drawn that these two surfaces are optically the same. If the two first signals continue to deviate from each other, then this allows the conclusion to be drawn that the indices of refraction differ. In this way, a conclusion about an index of refraction of the respective surface may be drawn on the basis of several measurements.

In a further embodiment it would also be possible that both measurement devices use both the same radiation device and the same radiation detection device. In this approach, however, depending on the particular measurement method used, either different diaphragms or diaphragms located at different positions would be used or would be programmed differently in the case of a locally resolved receiver.

Preferably, the first radiation device and the second radiation device direct the radiation onto the same area of the material or the surface. This would allow an accurate comparability of the two measurement results to be achieved.

In a further preferred embodiment, the apparatus includes a control unit which causes the first measuring device and the second measuring device to carry out measurements at different points in time. For example, it would be possible here that two different measurement values are taken one immediately after the other by the first and the second measuring device, in order to achieve in this way an accurate comparability of the measurement results.

It would also be possible that the entire apparatus is movable with respect to the surface to be examined and that during a standstill of the apparatus with respect to the surface two consecutive measurements are carried out. In a further advantageous embodiment, the apparatus comprises a housing which accommodates both the radiation device and the radiation detection device, and this housing just has one opening through which both radiation devices illuminate the material. In this embodiment it is achieved that the measurement result is distorted as little as possible by any external foreign light.

In a further advantageous embodiment, the radiation detection devices are arranged in such a way that the measurements of both measuring devices are in the same plane. In other words, the plane of the optical path of the beam directed onto the surface by the first radiation device and returning from the surface back to the radiation detection device is the same as the one formed by the beam which falls onto the surface from the second radiation device and is subsequently scattered back from the surface onto the second radiation detection device. However, the measurements could also be carried out in different planes.

Preferably, a filter corresponding to a $v_\lambda$ function is positioned in the beam path between the surface and the radiation detection device.

The present invention is further related to a method for determining optical properties of materials, wherein a first measuring device directs radiation by means of a first radiation device under a first specified angle of radiation onto the material and receives, by means of a first radiation detection device located under a first angle of reception with respect to the material, at least a proportion of the radiation directed onto the material by the first radiation device and scattered back from the material. In doing so, the first radiation detection device emits a first characteristic signal which is characteristic of an intensity of the radiation incident on the first radiation detection device and which preferably describes the imaging qualities of the surface.

According to the invention, a second measuring device directs radiation onto the material under a second specified angle of radiation by means of a second radiation device, and at least a proportion of the radiation directed onto the material by the first radiation device and scattered back from the material is received by a second radiation detection device which is located under a second angle of reception with respect to the material, wherein a second radiation detection device allows a locally resolved evaluation of the radiation incident thereon and emits at least one second characteristic signal which is characteristic of the radiation incident on the second radiation detection device.

The term "locally resolved observation of the radiation" as used herein is to be understood to mean that not only an intensity value is output in an integrated manner, but the radiation is differentiated across a certain area or at least two points or areas of different intensity can be distinguished. This may be carried out for example by using COD chips in the camera as the radiation detection device, which output locally resolved images. Thus, the image of the primary diaphragm (the diaphragm between the radiation device and the surface) may be examined with regard to distortion, expansion, reduction or tilting.

The radiation is preferably visible light and particularly preferably standardised white light. It would, however, also be possible to provide two radiation devices which output light of different wavelengths, so that the two measurements will not affect each other not even for example in the case of a partial simultaneousness.

In a further preferred method, at least one value which is characteristic of the material is output, taking into account the first signal and the second signal.

Preferably, measurements by the first measuring device and measurements by the second measuring device are carried out at different points in time. In this way it may be avoided that the measurements affect or interfere with each other. To this end it would be possible to use clocked light sources or to trigger the radiation device and the radiation detection device always in synchronism with each other.

According to a further advantageous method, measurements by the first measuring device and measurements by the second measuring device are carried out on essentially the same areas of the material or the surface.

BRIEF DESCRIPTION OF THE DRAWINGS

Further advantages and embodiments will become evident from the attached drawings, wherein:

FIG. 1 shows a schematic view of a first measurement method;

FIG. 2a shows a schematic illustration of a second measurement method;

FIG. 2b shows an illustration of an image taken by means of the second measurement method; and FIG. 3 shows a schematic illustration of an apparatus according to the invention.

DETAILED DESCRIPTION OF THE INVENTION

FIG. 1 shows a schematic view of a first measurement variant, or more precisely, a so-called gloss measurement. In this case, a first radiation device 4 is provided, which directs radiation onto the surface 10. The radiation S1 scattered back from the surface 10 is projected onto a first radiation detection device 6. This first radiation detection device 6 outputs an integral value for the incident intensity. Upstream of this first radiation detection device 6, a diaphragm 9 is located. This measurement variant preferably includes an essentially collimated beam path and therefore constitutes a gloss measurement. Correspondingly, the reference numeral 32 relates to a diaphragm and the reference numeral 34 relates to a lens disposed downstream of this diaphragm 32, which are used in combination for generating collimated light. A lens 36 is provided also on the reception side.

The diaphragm or the diaphragm image is projected here across the surface and the lenses onto the radiation detection device 6, with the radiation passing through the diaphragm 9 being integrally detected. This gloss measurement method is preferably carried out at 20°, 60° and 85°. The diaphragm apertures are established in corresponding standards.

It can be seen that depending on the property of the surface, not all of the light will reach the radiation detection device 6, but will be scattered in all directions in a manner similar to a radiation lobe K. In this way, a conclusion with regard to the quality or the gloss of the surface 10 may be drawn also on the basis of the ratio between the radiation reaching the radiation detection device 6 and the radiation incident on the surface 10. As mentioned above, the diaphragm 9 may also be realised as a software diaphragm.

FIG. 2a illustrates a second measurement method. Here, a radiation device 14 is provided, which directs radiation S2 onto a surface 10 or the material to be examined. This radiation S2 is reflected on the surface 10 and reaches a radiation detection device or an image reception device 16. The reference numeral 38 relates to a lens.

The reference numeral 8 relates to a diaphragm unit which is here located downstream of the second radiation device 14. This diaphragm unit 8 is projected across the surface 10 onto the radiation detection device 16. If structures are present on the surface, part of the light radiated onto the surface 10 will not be accurately reflected and therefore a blurred image will be received.

On the basis of a ratio between a scattered proportion reaching the radiation detection device 16 in the outer area and the overall radiation reaching the radiation detection device 16, a value for the dullness of the surface 10 may be output. This ratio is shown in FIG. 2b. The scattered proportion D1 is that proportion which lies within the outer ring segment, and the proportion D2 which is not or only to a lesser degree scattered around the area, is located in the centre of the image.

Thus, the radiation detection device here is a radiation detection device which allows a locally resolved radiation and is able to distinguish at least between those areas D1 and D2. For the evaluation, however, also a histogram of the pixel brightness could be used.

The value for the dullness as determined here may also be used for a value describing the DOI (Distinctiveness of Image) of the surface 10. It is possible here to use a further method to determine a surface structure of a surface, wherein, as mentioned above, this structure may be resolved as a function of different wavelength ranges. The DOI is subsequently obtained as a function of the dullness shown here and of two wavelength ranges in the near field. This is illustrated in detail in the above-mentioned Patent Application DE 10 2006 032 404 A1.

This DOI measurement is based on the realisation that surfaces may be perceived differently from different distances of observation. Thus, for example, any slight unevenness may be perceived only from a very close range. By contrast, for example, structures occurring at relatively large wavelengths may not be perceived when observed from close range, but may well be perceived when observing from a greater distance. These different distances may be simulated when different wavelength ranges are considered. Such DOI measurements are also taken by means of a locally resolved detection device such as a camera or a COD chip.

The method shown in FIG. 1 is, however, as was mentioned above, relatively sensitive with respect to curvatures of the surface 10. By contrast, the method used for DOI measurements is relatively insensitive with respect to curvatures of the surface.

The proportion of the backscattered radiation in the measurement method shown in FIG. 1 is also dependent on the index of refraction of the respective material. By contrast, the measurement illustrated in FIG. 2 is not dependent on the index of refraction.

Moreover, it is to be taken into account that different paint systems known in the prior art, for example water-based or solvent-based paints, may also have different indices of refraction, which, although optically equivalent, may affect the measurement illustrated in FIG. 1. In FIG. 2a it would also be possible to set up two sensors instead of a camera or a CCD chip, with one sensor being formed for example in a circular shape on the inside and the second sensor surrounding this first sensor in a ring-like fashion. In this case, however, tracking of the diaphragms in a case of tilting is no longer possible. The measurement method shown in FIG. 2a in turn requires a comparatively high proportion of the reflection of the surfaces to be examined.

FIG. 3 shows a schematic view of an apparatus 1 according to the invention. This apparatus comprises a housing 20 in which a first measuring device generally identified with 2 and a second measuring device generally identified with 12 are located. This housing 20 is essentially sealed and has only one opening 22 through which a surface 10 may be inspected.

The first measuring device 2 has here a first radiation device 4 and a first radiation detection device 6. The first radiation device 4 and the first radiation detection device 6 are here symmetrically arranged with regard to a mean perpendicular M, i.e. the light reflected onto the surface 10 and from the surface 10 reaches the radiation detection device 6.

The reference numeral 14 relates to a second radiation device which is part of the second measuring device 12. Apart from that, this second measuring device 12 has a second radiation detection device 16, and here, too, the second radiation device 14 and the second radiation detection device 16 are arranged symmetrically in relation to the mean perpendicular M. It would, however, also be possible for the second radiation detection device 16 not to be positioned within the angle of reflection with regard to the second radiation device 14, but to be offset in relation thereto. It is possible here to extrapolate measurement results obtained under different angles. Or to be more precise, the diaphragm may be tracked here for evaluation.

In the arrangement shown in FIG. 3, the second measuring device 12 is positioned within the first measuring device 2 with respect to the mean perpendicular M, since steeper measurement angles are more suitable for the second measurement method than for the first measurement method.

Preferably, however, the individual radiation devices 4, 14 as well as the individual radiation detection devices 6, 16 are arranged in such a way that the individual measurements will not affect each other, i.e. light from the first radiation device 4 will not reach the second radiation detection device 16, nor will light from the second radiation device 14 reach the first radiation detection device 6.

The reference numeral 24 relates to a processing device which stores the signals or measurement values output from the two radiation detection devices 6, 16 and which outputs a characteristic measurement value for the surface 10 on the basis of these measurement values. Moreover, the apparatus also includes a memory device 26 in which the first signal values that are characteristic of different indices of refraction may be stored. In this way, a conclusion may be drawn with regard to an index of refraction of the respective material on the basis of a comparison made between from the first and the second radiation detection devices 6, 16.

By means of a control device 28 it may be achieved that measurements may be carried out by the two measuring devices 2, 12 in a temporally offset manner, so that these measurements will not affect each other.

It is further possible that the apparatus generally identified with 1 includes dislocation elements such as wheels in order to move the apparatus with respect to a surface such as the body of a vehicle. To this end, also distance measuring devices 40 may be provided which determine the distance covered by the apparatus with respect to the surface. It would also be possible to position the apparatus according to the invention for example on a robot arm and to move this across the surface to be examined.

It would also be possible to correlate the measurement values obtained by the two measuring devices 2, 12 with the distance values output by the distance measuring device. In this way, the values determined by the first measuring device 2 and the second measuring device 12 could be allocated to certain locations on the surface 10, and in addition, this would make it easier to carry out measurements also during a movement of the apparatus 1 with respect to the surface 10. For example, measurements could be initiated at certain positions of the apparatus 1 with respect to the surface 10, for example at regular intervals with regard to one another.

Apart from that, the two measuring devices 2, 12 may include further optical elements such as in particular lenses which are located in the respective beam paths. The reference numeral 8 relates to a diaphragm unit which is part of the second measuring device. This diaphragm unit 8 may be adjustable with regard to its aperture. The reference numeral 9 identifies a further diaphragm unit which is part of the first measuring device. In principle it would also be possible that both measuring devices 2, 12 each use a common radiation device and/or a common radiation detection device. In this connection it is preferred that the diaphragm 8 is repositioned depending on the measurement method. If the diaphragm 9 is a diaphragm realised by software, then this may also be readily "removed" for the measurement method described in FIG. 2.

All of the features disclosed in the application materials are claimed as essential to the invention, in as far as they are novel compared to the prior art either individually or in combination.

| List of Reference Numerals | |
|---|---|
| 1 | Apparatus |
| 2 | First Measuring Device |
| 4 | First Radiation Device |
| 6 | First Radiation Detection Device |
| 8 | Diaphragm Unit |
| 9 | Diaphragm Unit |
| 10 | Surface |
| 14 | Second Radiation Device |
| 16 | Second Radiation Detection Device |
| 20 | Housing |
| 22 | Opening in the Housing |
| 24 | Processing Means |
| 26 | Memory Device |
| 28 | Control Unit |
| 32 | Diaphragm Unit |
| 34 | Lens |
| 36, 38 | Lenses |
| S1, S2 | Radiation, Beam Path |
| D1, D2 | Distance |
| K | Radiation Lobe |
| M | Mean Perpendicular |

The invention claimed is:

1. An apparatus for determining optical properties of a material, comprising a first measuring device having a first radiation device which directs radiation onto the material under a first specified angle of radiation and which includes a first radiation detection device which is located under a first angle of reception with respect to the material and which receives at least a proportion of the radiation directed onto the material by the first radiation device and scattered back from the material, with the first radiation detection device emitting a first characteristic signal which is characteristic of an intensity of the radiation incident on the first radiation detection device,
wherein
the apparatus further comprises a second measuring device which includes a second radiation device which directs radiation onto the material under a second specified angle of radiation and which includes a second radiation detection device which is located at a certain second angle of reception with respect to the material and which receives at least a proportion of the radiation directed onto the material by the second radiation device and scattered back from the material, with the second radiation detection device allowing a locally resolved evaluation of the radiation incident thereon which is characteristic of an intensity value output in an integrated manner, which radiation is differentiated across a certain area or at least two points or areas of different intensity can be distinguished, and emitting at least one second characteristic signal which is characteristic of the radiation incident on the second radiation detection device, wherein the apparatus has a processor which outputs a value which is characteristic of the material, taking into account the first characteristic signal and the second characteristic signal by comparing both signals with each other, wherein at least first signal values are characteristic of different indices of refraction and in this way a conclusion as to a dullness or gloss of the material is drawn with regard to an index of refraction of the respective material on a basis of said comparison.

2. The apparatus as claimed in claim 1, wherein the first angle of radiation and a first angle of reception are essentially mirror-inverted with regard to a mean perpendicular extending in relation to the material.

3. The apparatus as claimed in claim 1, wherein the material is a surface.

4. The apparatus as claimed in claim 1, wherein the apparatus includes a radiation detection device which is part of both the first and the second measuring devices.

5. The apparatus as claimed in claim 1, wherein the apparatus includes a radiation device which is part of both the first and the second measuring devices.

6. The apparatus as claimed in claim 1, wherein a diaphragm unit is positioned upstream of the first radiation detection device.

7. The apparatus as claimed in claim 1, wherein the first radiation device and the second radiation device direct the radiation onto a same area of the material.

8. The apparatus as claimed in claim 1, wherein the apparatus includes a control unit which causes the first measuring device and the second measuring device to carry out measurements at different points in time.

9. The apparatus as claimed in claim 1, wherein the apparatus includes a housing in which both the radiation devices and the radiation detection devices are located, said housing having just one opening through which both radiation devices illuminate the material.

10. The apparatus as claimed in claim 1, wherein distance values are output and wherein the processor correlates measurement values obtained by the two measuring devices with the distance values.

11. The apparatus as claimed in claim 1, wherein tables are created or taken as a basis by the processor, to allocate corresponding indices of refraction to certain first signals, wherein the respectively second signal is taken into account for the allocation.

12. The apparatus as claimed in claim 1, wherein the radiation detection devices are arranged so that light from a first radiation device will not reach the second radiation device, and vice versa.

13. The apparatus as claimed in claim 1, wherein the first and second measuring devices are temporally offset from one another so that individual measurements of the first radiation device will not affect the second radiation device, and vice versa.

14. The apparatus as claimed in claim 1, wherein the second characteristic signal is analysed under determination of several different factors.

15. The apparatus as claimed in claim 14, wherein the processor emits a value characteristic of an index of refraction of the material, taking into account the first characteristic signal and the second characteristic signal.

16. A method for determining optical properties of a material, wherein a first measuring device directs radiation by means of a first radiation device onto the material under a first specified angle of radiation and receives, by a first radiation detection device which is located under a first angle of reception with respect to the material, at least a proportion of the radiation directed from the first radiation device onto the material and scattered back from the material, the first radiation detection device emitting a first characteristic signal which is characteristic of an intensity of the radiation incident on the first radiation detection device, wherein a second measuring device directs radiation onto the material under a second specified angle of radiation by means of a second radiation device and receives, by a second radiation detection device which is located at a second angle of reception with respect to the material, at least a proportion of the radiation directed onto the material by the first radiation device and scattered back from the material, with the second radiation detection device allowing a locally resolved evaluation of the radiation incident thereon which is characteristic of an intensity value output in an integrated manner, which radiation is differentiated across a certain area or at least two points or areas of different intensity can be distinguished, and emitting at least one second characteristic signal which is characteristic of the radiation incident on the second radiation detection device, wherein on a basis of taking into account the first characteristic signal and/or the second characteristic signal, at least one value which is characteristic of the material is output by comparing both signals with each other, wherein at least first signal values are characteristic of different indices of refraction and in this way a conclusion as to a dullness or gloss of the material is drawn with regard to an index of refraction of the respective material on the basis of said comparison.

17. The method as claimed in claim 16, wherein measurements of the first measuring device and measurements of the second measuring device are carried out at different points in time.

18. The method as claimed in claim 16, wherein measurements of the first measuring device and measurements of the second measuring devices are carried out on essentially same areas of the material.

19. The method as claimed in claim 16, wherein according to at least one method, at least two detector areas are evaluated and are used for determining a measurement value in relation to each other in a predetermined ratio.

20. The method as claimed in claim 16, wherein measurement values obtained by the first and second measuring devices are correlated with outputted distance values.

21. The method as claimed in claim 16, wherein tables are created or taken as a basis which allocates corresponding indices of refraction to certain first signals, wherein the respectively second signal is taken into account for the allocation.

* * * * *